(12) United States Patent
Kolluri et al.

(10) Patent No.: US 7,288,070 B2
(45) Date of Patent: Oct. 30, 2007

(54) METHOD AND APPARATUS FOR DETERMINING EXTREME BLOOD PRESSURE VALUES

(75) Inventors: Sai Kolluri, Tampa, FL (US);
Lawrence T. Hersh, Tampa, FL (US);
Bruce Friedman, Tampa, FL (US);
Richard Medero, Tampa, FL (US)

(73) Assignee: The General Electric Company, Schenactady, NY (US)

( * ) Notice: Subject to any disclaimer, the term of this patent is extended or adjusted under 35 U.S.C. 154(b) by 470 days.

(21) Appl. No.: 10/847,934

(22) Filed: May 18, 2004

(65) Prior Publication Data
US 2005/0261597 A1  Nov. 24, 2005

(51) Int. Cl.
*A61B 5/02* (2006.01)
*A61B 5/04* (2006.01)

(52) U.S. Cl. ............... 600/493; 600/485; 600/490; 600/500; 600/509

(58) Field of Classification Search .......... 600/493, 600/495
See application file for complete search history.

(56) References Cited

U.S. PATENT DOCUMENTS

| | | | |
|---|---|---|---|
| 4,360,029 A | 11/1982 | Ramsey, III | |
| 4,543,962 A | 10/1985 | Medero et al. | |
| 4,638,810 A | 1/1987 | Ramsey, III et al. | |
| 4,796,184 A | 1/1989 | Bahr et al. | |
| 4,889,133 A | 12/1989 | Nelson et al. | |
| 4,949,710 A | 8/1990 | Dorsett et al. | |
| 5,579,776 A | 12/1996 | Medero | |
| 5,704,362 A | 1/1998 | Hersh et al. | |
| 5,797,850 A | 8/1998 | Archibald et al. | |
| 5,865,756 A * | 2/1999 | Peel, III | 600/490 |
| 6,358,213 B1 | 3/2002 | Friedman et al. | |
| 6,423,010 B1 | 7/2002 | Friedman et al. | |
| 6,440,080 B1 | 8/2002 | Booth et al. | |
| 2002/0082507 A1 | 6/2002 | Kolluri et al. | |

OTHER PUBLICATIONS

U.S. Appl. No. 10/387,631, filed Mar. 31, 2003, Medero et al.
Non-invasive automatic determination of mean arterial pressure, Maynard Ramsey III, Medical & Biological Engineering & Computing, 1979, 17, 11-18.
Blood Pressure Monitoring: Automated Oscillometric Devices, Maynard Ramsey III, Journal of Clinical Monitoring, vol. 7, No. 1, Jan. 1991, 56-67.

* cited by examiner

*Primary Examiner*—Charles A. Marmor, II
*Assistant Examiner*—Patricia Mallari
(74) *Attorney, Agent, or Firm*—Andrus, Sceales, Starke & Sawall, LLP (57) ABSTRACT

In a method and apparatus for measuring extreme blood pressure values during a single non-invasive blood measurement, the time intervals between sequential heartbeats are measured for a series of heartbeats in an oscillometric blood pressure measurement time period. Oscillometric blood pressure measurement data for the heartbeats of the series is obtained and associated with the heartbeat time intervals. An average time interval between heartbeats is also determined. A first data bin may be defined for blood pressure data associated with time intervals that are longer as compared to the average time interval. A second data bin is defined for blood pressure data with time intervals that are shorter as compared to the average time interval. The measured oscillometric blood pressure data is sorted into the data bins in accordance with the associated time intervals. The data in the first data bin is used to derive a high systolic blood pressure value and a low diastolic blood pressure value. The data in the second bin is used to derive a low systolic blood pressure value and a high diastolic blood pressure value. A typical blood pressure value may also be determined.

41 Claims, 5 Drawing Sheets

Fig. 3 Plot of $Sys_{n+1}$ vs. $T_n$

Fig. 5 Plot of $(Sys_{n+1} - Dias_n)$ vs. $T_n$

Fig. 4 Plot of $Dias_n$ vs. $T_n$

Fig. 6 Plot of $Sys_{n+1}$ vs. $T_n$ on a different patient

METHOD AND APPARATUS FOR DETERMINING EXTREME BLOOD PRESSURE VALUES

BACKGROUND OF THE INVENTION

The present invention relates to a method and apparatus capable of non-invasively determining the highest and lowest values for systolic and diastolic blood pressures, as well as a typical blood pressure value. While not so limited, the method and apparatus of the present invention is particularly useful for obtaining the foregoing blood pressure measurements from patients in which blood pressures vary significantly from heartbeat to heartbeat, such as patients in atrial fibrillation. The determination may be carried out in a single non-invasive blood pressure measurement procedure.

The determination of blood pressure is a basic physiological measurement. It indicates the forces exerted on the blood vessels of the circulatory system by the pumping, or beating, action of the heart. The repeated pumping action of the heart causes the pressure within the blood vessels to cyclically increase and decrease. Blood pressure is typically expressed in terms of the highest pressure observed during a cycle and the lowest level of pressure observed during a cycle. The former is termed "systolic" pressure, the latter is termed the "diastolic" pressure, and the indication of blood pressure at the end of a measurement procedure is commonly expressed as a combination of the two pressures, i.e. "110/70" or "110 over 70", it being understood that the units of pressure are millimeters of mercury (mm Hg).

Blood pressure may be determined by means of auscultation, in which a blood vessel, typically the brachial artery in the upper arm, is occluded by a pressurized cuff, and the sounds of the blood moving through the blood vessel are detected with a stethoscope as the pressure in the cuff is reduced. The cuff pressures at appearance and disappearance of these sounds as the cuff is deflated from the occluding state are indications of the systolic and diastolic pressures. Or, blood pressure can be measured by an oscillometric technique in which a blood vessel is occluded and the magnitude of the pulsations of the blood in the blood vessel is measured as the pressure in the cuff is lessened. The pattern of increase and decrease in oscillation size as the cuff pressure changes can be used to estimate systolic, mean arterial, and diastolic blood pressures. Oscillometry is often used in blood pressure monitors because it lends itself to being carried out by automated instrumentation.

For auscultation, the values that are presented for the systolic and diastolic blood pressures depend, to a considerable extent on the skill and predilection of the clinician, whereas for oscillometry, the reported values are based on the assumptions and structure built into the instrumentation algorithm. In both cases, the expressed systolic and diastolic pressures values are commonly thought of as being found in each of a succession of heartbeats occurring over an extended period of time. This permits such blood pressure values to serve as a basis for screening and treatment. But as a result, extreme values may not be fully reflected in the blood pressure determination because of an effort to provide what is seen as the most representative, and generally more useful, blood pressure values.

However, as noted above, there are medical conditions in which a patient's blood pressure is changing by large amounts on almost every beat of the heart. One such condition is irregularity in the rhythms of the heartbeat, such as is found in patients with atrial fibrillation. In these patients, it is clinically significant not only to know typical blood pressure values, but also to know the extremes, i.e. highest and lowest systolic and diastolic blood pressure values seen in the patient.

BRIEF DESCRIPTION OF THE INVENTION

An embodiment of the invention is, therefore, directed to methods and apparatus for accurately determining typical and, particularly, extremes in blood pressure values.

Briefly, the present invention relates to a method and apparatus for obtaining at least one blood pressure value of interest from a non-invasive blood pressure measurement using an oscillometric technique. The functioning of the heart is analyzed to obtain physiological data suitable for identifying, in a series of heartbeats in the measurement time period, those heartbeats having blood pressure properties of interest from heartbeats not having blood pressure properties of interest. Oscillometric blood pressure measurement data for the heartbeats of the series is obtained and associated to the physiological data. At least one criterion for the physiological data is established that identifies heartbeats in the series of heartbeats having the blood pressure properties of interest. By applying the criterion to the physiological data, oscillometric blood pressure measurement data for which the associated physiological data meets the criterion is accumulated and used to derive at least one blood pressure value of interest.

Briefly, in another embodiment of the method and apparatus of the present invention, the time intervals between sequential heartbeats are measured for a series of heartbeats in an oscillometric blood pressure measurement time period. Oscillometric blood pressure measurement data for the heartbeats of the series is obtained and associated with the heartbeat time intervals. An average time interval between heartbeats is determined. Typically, determination of the average time interval will use the time intervals between the sequential heartbeats occurring in the blood pressure measurement time period so as to enable the blood pressure value determination to be carried out in a single non-invasive blood pressure measurement procedure. However, if desired, a predetermined number of heartbeats may be employed that may include heartbeats occurring outside the blood pressure measurement time period so as to provide an adequate sample of heartbeat data.

Data bins are defined for the measured oscillometric blood pressure data using properties of the associated time intervals. For example, a first bin may be defined for blood pressure data associated with time intervals that are longer as compared to the average time interval. A second data bin is defined for blood pressure data with time intervals that are shorter as compared to the average time interval. The measured oscillometric blood pressure data is sorted into the data bins in accordance with the associated time intervals.

The data in the first data bin is used to derive a high systolic blood pressure value and a low diastolic blood pressure value. The data in the second bin is used to derive a low systolic blood pressure value and a high diastolic blood pressure value. The blood pressure values so derived are displayed or otherwise employed in a blood pressure monitor or other apparatus. Typical blood pressure values obtained from the oscillometric blood pressure measurement data may also be displayed.

Criteria other than heartbeat time interval may be used to establish the bins. For example, ECG morphology or oscillometric pulse shape may be used for this purpose.

If data of a sufficient amount and adequate quality for the determination of extreme values is not available from a single non-invasive blood pressure measurement procedure, data from multiple procedures may be used.

BRIEF DESCRIPTION OF THE DRAWINGS

The invention will be further understood by reference to the following detailed description taken in conjunction with the attached drawing in which.

DETAILED DESCRIPTION OF THE INVENTION

Figure 1:
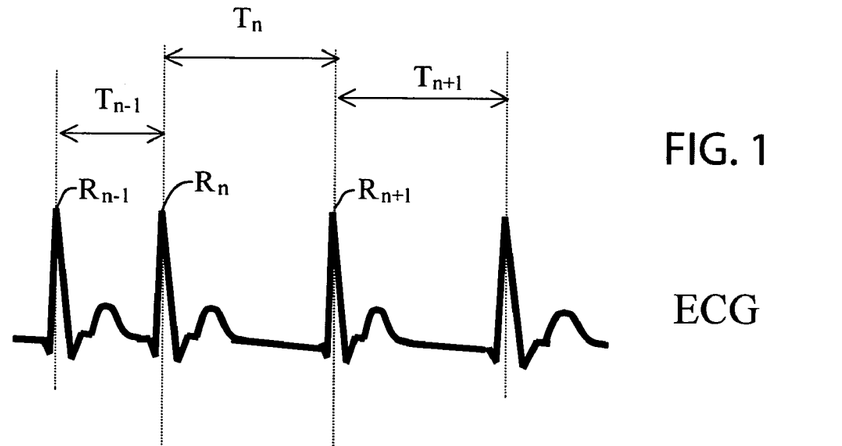
FIG. 1 shows an electrocardiographic signal for a patient exhibiting irregular heartbeat rhythm.

FIG. 1 shows a graph of an electrocardiograph (ECG) signal obtained from a patient and reflecting the physiological functioning of the heart. Each beat of the heart features a peak value $R_{n-1}$, $R_n$, $R_{n+1}$, associated with the contraction of the heart that is useful in determining the time interval T between the beats. The data shows an irregular heartbeat in which the time intervals $T_{n-1}$, $T_n$, $T_{n+1}$, etc. between beats vary in duration.

Figure 2:
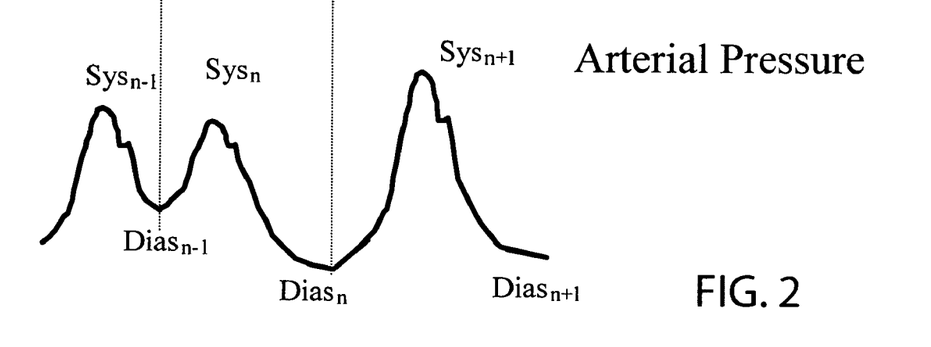
FIG. 2 shows corresponding arterial blood pressure data.

FIG. 2 shows systolic and diastolic arterial blood pressures for the heartbeats shown in FIG. 1. For the first heartbeat shown in FIG. 1, the pressure $Sys_{n-1}$ is the systolic, or high, pressure resulting from the beat of the heart that was produced after the ECG waveform $R_{n-1}$. Pressure $Dias_{n-1}$ is the diastolic, or low, pressure seen at the end of the time interval $T_{n-1}$.

Figure 3:
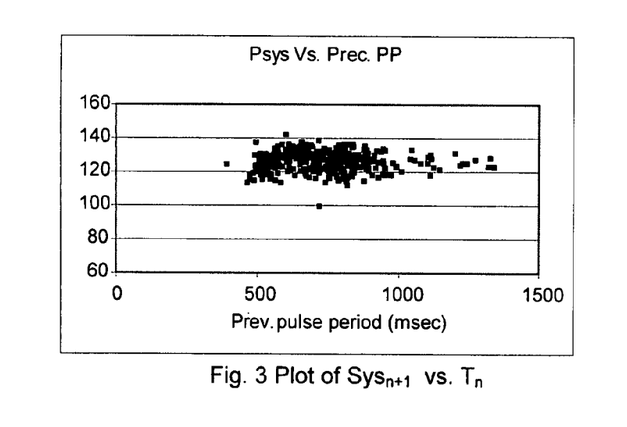
FIG. 3 is a plot relating systolic blood pressure to the length of the preceding heartbeat time interval.

As noted in the introductory portions of this specification, for patients exhibiting irregular heartbeat rhythms, there are changes in blood pressures on almost every heartbeat, and often by large amounts. FIG. 3 shows a plot of systolic blood pressure values Sys as compared to heartbeat time intervals T. Specifically, FIG. 3 shows a plot of systolic blood pressure values (Psys) as compared to the previous heartbeat time interval $T_n$. It thus relates a systolic blood pressure value, such as $Sys_{n+1}$ shown in FIG. 2 to the time interval to the previous heartbeat $T_n$ shown in FIG. 1. The values shown in FIG. 3, as well as those shown in FIGS. 4-6 where obtained from an invasive blood pressure recording taken directly from a blood vessel of the patient.

From the data shown in FIG. 3, it can be said that for that patient systolic blood pressure remains somewhat uniform as the time interval between heartbeats varies. That is, the pattern of the plots shown in FIG. 3 is generally horizontal at a blood pressure of around 130 mm Hg as the time interval between heartbeats varies from 500 to approximately 1300 ms, corresponding to 120 to 46 beats per minute.

Figure 6:
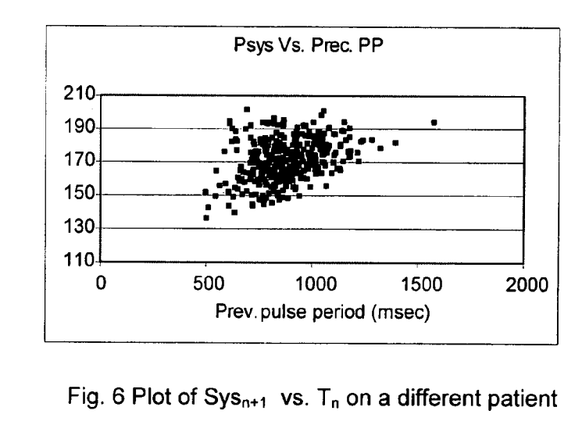
FIG. 6 is a plot, similar to FIG. 2, relating systolic blood pressure to the length of the preceding heartbeat time interval, but for a different patient.

The same is not true for the patient presenting the data shown in FIG. 6. For that patient, as the time interval between heartbeats increases, the systolic pressure also generally increases.

Figure 4:
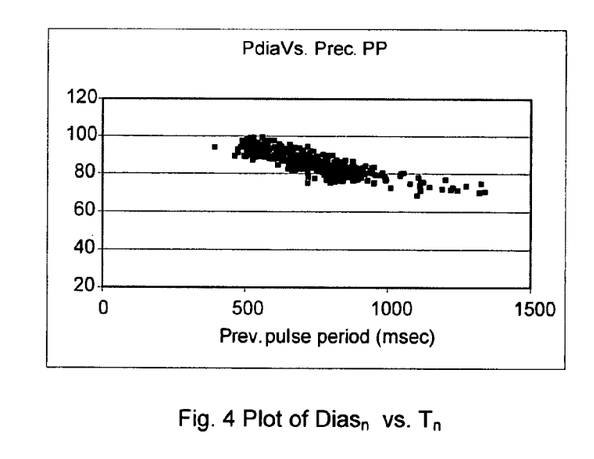
FIG. 4 is a plot showing diastolic blood pressure data and the time interval between heartbeats.

The variation in blood pressures as a function of the time interval between heartbeats is also apparent from the diastolic pressure data shown in FIG. 4 in which diastolic pressure tends to decrease as the time interval between heartbeats increases.

Figure 5:
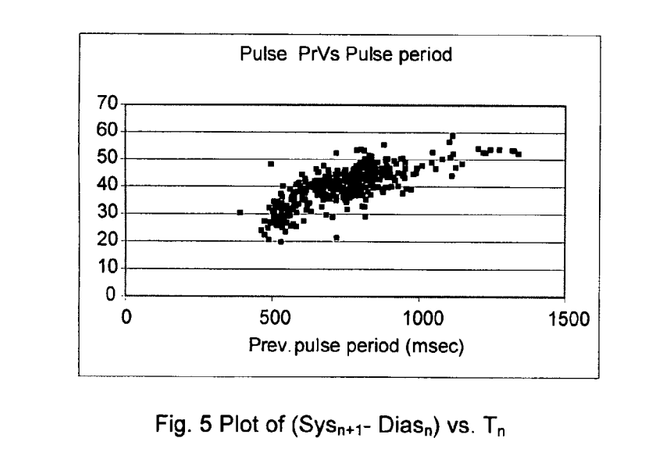
FIG. 5 is a plot showing the difference between a systolic blood pressure and the previous diastolic blood pressure as related to a heartbeat time interval.

FIG. 5 relates the pressure difference between the systolic pressure and the previous diastolic blood pressure to the preceding time interval between the heartbeats. It thus shows the difference between a systolic pressure $Sys_{n+1}$ and the previous end-diastolic pressure $Dias_n$ to the time interval $T_n$ for the heartbeat previous to the given heartbeat. FIG. 5 clearly shows that one or both of the systolic and diastolic pressures become more extreme, i.e. the pressure difference increases, as the time interval between heartbeats becomes greater. The pressure difference and extremes in values are also shown, somewhat diagrammatically, in FIG. 2 in which, for example, the pressure difference between values $Sys_{n+1}$ and $Dias_n$ is greater than the difference between values $Sys_n$ and $Dias_{n-1}$. The longer time interval $T_n$ is associated with the former pressure difference whereas the shorter time interval $T_n$ 1 is associated with the latter difference. The pressure difference shown in FIG. 5 is reflected in the amplitude of the blood pressure oscillation measured during an oscillometric blood pressure determination hereinafter described.

Figure 7:
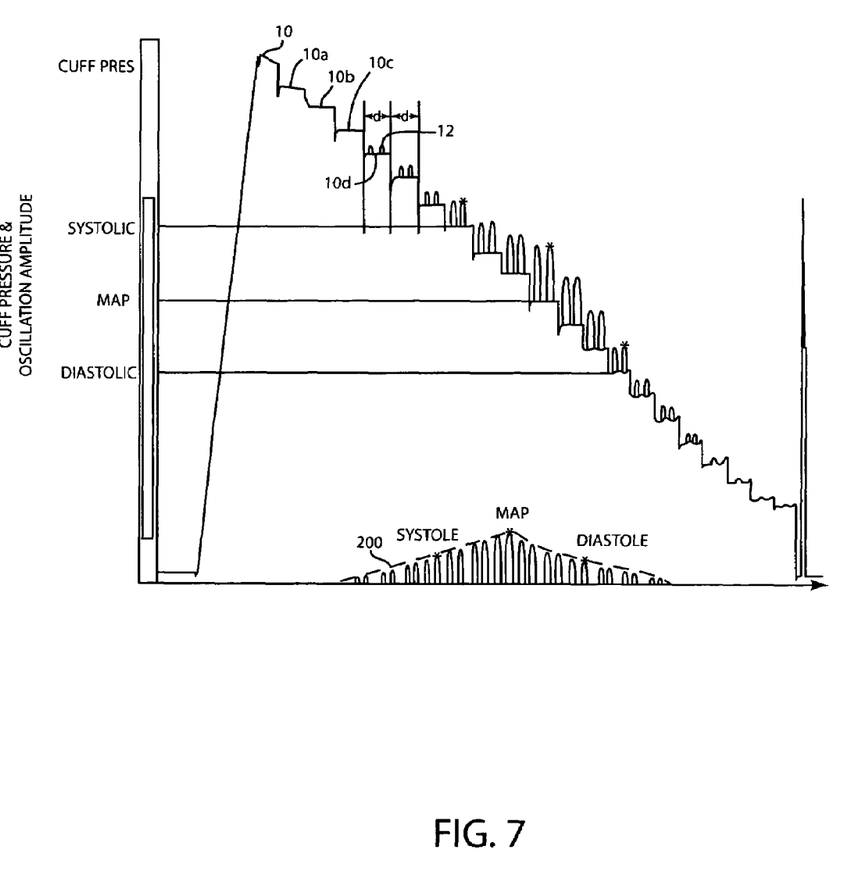
FIG. 7 is a graph illustrating the oscillometric technique for non-invasive blood pressure measurement.

FIG. 7 shows the measurement of blood pressure using the oscillometric technique. An occluding cuff is inflated to a pressure 10 sufficient to occlude an arterial blood vessel surrounded by the cuff. Thereafter, the cuff is deflated in a step-like manner, as shown by pressures 10a, 10b, 10c. As the pressure of the cuff decreases, at some point, the peak systolic blood pressure 12 produced by the pumping action of the heart will exceed the pressure 10d of the cuff. This will allow the peak blood pressure to be sensed by a pressure sensor associated with the cuff. As the decremental deflation of the cuff proceeds, the magnitude of the pressure peaks (12) produced by the pumping action of the heart will increase and thereafter decrease as the decreasing cuff pressure lessens the occlusion of the blood vessel. The pressures produced by the pumping action of the heart are shown on the abscissa of the graph of FIG. 7 as an oscillometric envelope. An algorithm is applied to the oscillometric data obtained during the decremental deflation of the cuff to determine the systolic, mean arterial, and diastolic blood pressure values given. In connection with such determination, see for example, U.S. Pat. Nos. 4,360,029; 4,638,810; and 5,704,362, and co-pending U.S. patent application Ser. No. 10/387,631, filed Mar. 13, 2003 and assigned to a common assignee which is incorporated herein by reference.

Figure 8:
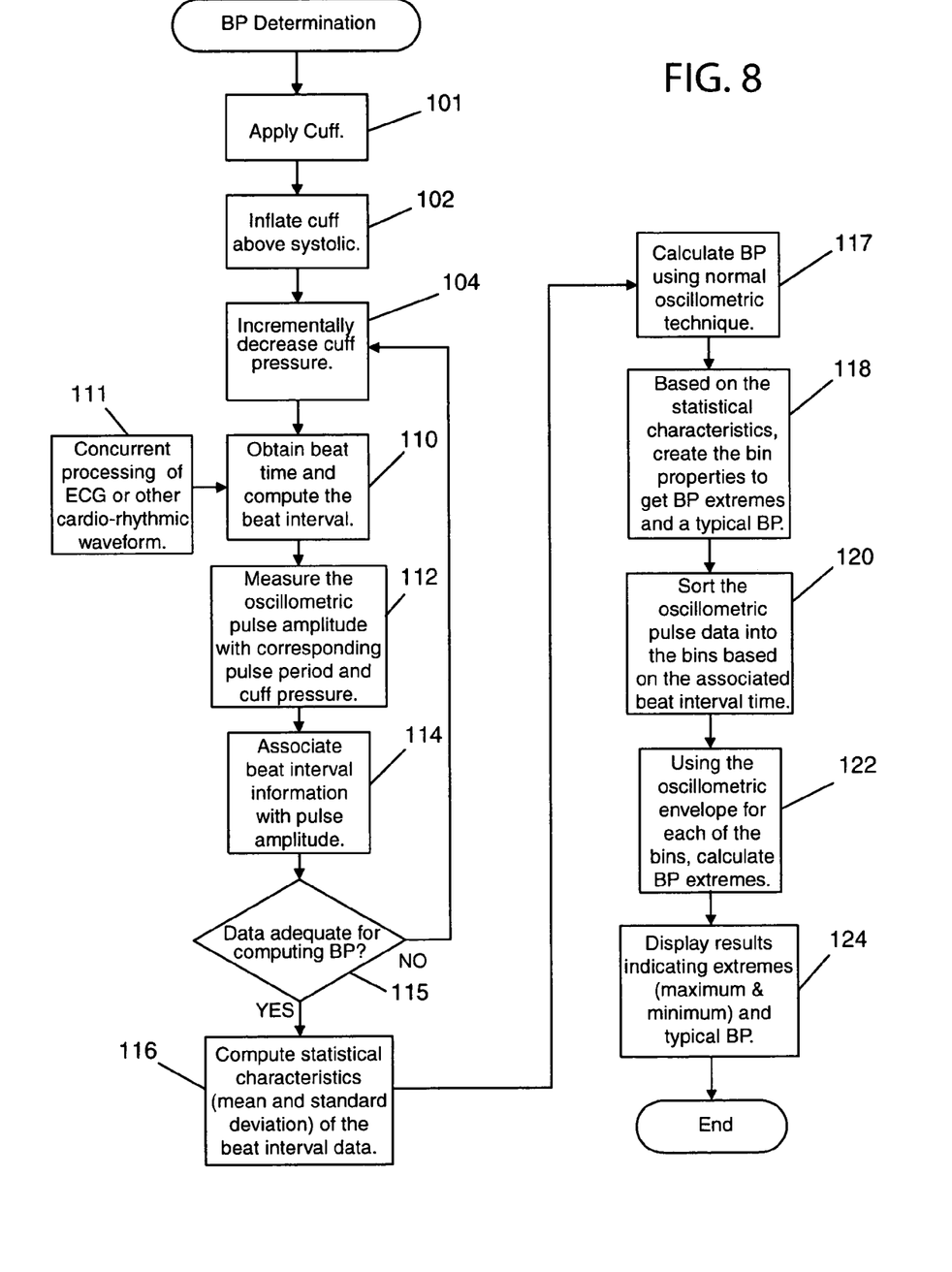
FIG. 8 is a flow chart illustrating an embodiment of the method of the present invention.

An embodiment of the method of the present invention is shown in the flow chart of FIG. 8. In a prefatory step 101, the inflatable cuff is applied to the body of the patient to surround the blood vessel to be used in blood pressure measurement.

Thereafter in a further prefatory step, the pressure in the inflatable cuff is increased at step 102 to an elevated pressure, such as that shown in FIG. 7 at 10, that is sufficient to occlude the blood vessel. In step 104, the pressure in the cuff is decrementally decreased, also in the manner shown in FIG. 7, to commence the oscillometric blood pressure measurement.

In the present invention, during the oscillatory blood pressure determination, the physiological functioning of the heart is analyzed to obtain data suitable for identifying heartbeats for which systolic and diastolic blood pressures have more extreme values from heartbeats for which the systolic and diastolic blood pressures are less extreme. Using the example shown in FIG. 2, what is desired is to be able to identify a heartbeat exhibiting the blood pressure value $Sys_{n+1}$ and $Dias_n$ from a heartbeat exhibiting the blood pressure values $Sys_n$ and $Dias_{n-1}$, the former having more extreme values (higher systolic and lower diastolic blood pressures) than the latter. As shown in FIGS. 1 and 5, a convenient way of determining this is to use the length of the time interval between sequential heartbeats: the time interval $T_n$ associated with the more extreme blood pressure values $Sys_{n+1}$ and $Dias_n$ being greater than the time interval $T_{n-1}$ associated with less extreme blood pressures $Sys_n$ and $Dias_{n-1}$.

While the use of time intervals is described below for exemplary purposes, other physiological phenomena may be used for the foregoing purpose, such as the ECG waveform structure or oscillometric pulse shape. For example, it is known that frequent premature ventricular contractions will lower blood pressures. It may therefore be desirable to analyze the ECG waveform morphology to identify heartbeats in which a premature ventricular contraction has occurred and those heartbeats in which such a contraction has not occurred. Techniques for analyzing ECG waveform morphology are described in literature such as *Marriot's Practical Electrocardiography* by Galen S. Wagner and Henry J. L. Marriott published 1972 ISBN 0683055720 and *Advanced Concepts in Arrhythmias* by Henry J. L. Marriott and Mary B. Conover published 1998 ISBN 0815120907. The analysis of oscillometric pulse morphology is described in the above noted U.S. Pat. No. 4,360,029 and patent application Ser. No. 10/387,631, and in U.S. Pat. No. 5,797,850.

Thus in the present invention, during the oscillometric blood pressure measurement, the time interval between sequential heartbeats for a series of heartbeats is measured in step 110. As noted in connection with FIG. 1, the time intervals between sequential heartbeats can be conveniently measured by ascertaining the time intervals between the peak R values of the electrocardiographic (ECG) waveform obtained, in step 111, from ECG electrodes applied to the patient. Other cardio-rhythmic waveforms may be used, if desired and as noted in FIG. 8.

Oscillometric blood pressure measurement data is also obtained for the heartbeats of the series of heartbeats in step 112. As shown in FIG. 7, this data consists of the various pressures 10a, 10b, etc. in the occluding cuff as the cuff pressure is decrementally decreased, as well as the pressure excursions 12, or pulses, of the blood pressure, produced by the action of the heart during each heartbeat.

The oscillometric blood pressure data is then associated or linked to heartbeat time interval data in step 114. As shown in connection with FIGS. 3-6, the oscillometric pulse amplitude found in a given heartbeat is typically linked to the previous heartbeat time interval. Other linkage arrangements may be used, if desired. The result of step 114 is a collection of data associating a heartbeat physiological indicator, such as the heartbeat time interval T, to oscillometric pulse 12 data.

In step 115, the oscillometric data, and preferably also the time interval data, is analyzed to ascertain that sufficient data is available to determine that the oscillometric waveform has the proper consistency, and that the data is artifact-free. Techniques for carrying out this step are described in the U.S. patent application and patents noted herein.

Assuming data is present in sufficient quantity and quality, the statistical characteristics of the beat interval data are then computed in step 116. In an explanatory example herein described, in step 116, an average or mean time interval between heartbeats is computed. The computation of this average may employ the time intervals between the heartbeats used to obtain the oscillometric blood pressure data. Or, the computation of the average may employ a given number of heartbeat intervals. For example, computation of the average may use the heartbeat time intervals for the measurement period plus an additional number of previous or subsequent heartbeat time intervals to comprise 120 data points.

Before carrying out the further steps of the method shown in FIG. 8, the blood pressure of the subject may be determined in step 117 in an ordinary or conventional oscillometric manner using the oscillometric pulse amplitude data obtained in step 112. This determination will provide a typical or representative indication using all the data collected in step 112.

Thereafter, the oscillometric blood pressure measurement data is sorted, or divided, based on the length of the associated heartbeat time intervals. In statistical analysis, such data processing is often described as sorting the data into "bins." In a simple example, the oscillometric data that is to be used to determine the blood pressure value or values are sorted or accumulated into a bin. For example, in step 118, a bin may be defined or established to contain oscillometric data for which the associated time interval has a length greater than or equal to the average time interval computed in step 116.

In a further example of the present invention, the oscillometric data may be sorted into two bins. Thus, in step 118, a first bin, bin 1, will be defined or established to contain oscillometric data for which the associated time interval has a length greater than or equal to the average time interval computed in step 116. A second bin, bin 2, will have the oscillometric blood pressure measurement data for which the associated heartbeat time interval is equal to or less than the average heartbeat interval determined in step 116. All the oscillometric data will thus be placed in at least one of the bins. It will be appreciated that some oscillometric blood pressure measurement data will be in both bins if the associated heartbeat time interval corresponds to the average heartbeat interval. However, additional data points assist in an accurate determination of blood pressure values in the technique of the present invention.

It will also be appreciated that it is possible to use more than two bins in sorting the oscillometric blood pressure measurement data. For example, thresholds such as the average time interval ±1 standard deviation (SD) or the average time interval ±2 SD could be used, the standard deviations being determined as a statistical characteristic of the beat interval data in step 116. The data sorting bins could then be such that a first bin would contain oscillometric blood pressure measurement data for which the associated time interval fell between the average time interval and the average time interval +1 standard deviation on one side of the average value, a second bin would contain oscillometric blood pressure measurement data for which the associated time interval was greater than the average time interval +1 standard deviation and bins 3 and 4 would be defined in a corresponding manner but on the other side of the average time interval.

In the following explanation, the description employs two data sorting bins. The sorting of the oscillometric blood pressure measurement data into bins 1 and 2 occurs in step 120. As a result of the data sorting, bin 1 contains blood pressure data for which the corresponding heartbeat time interval is greater than or equal to the average heartbeat to heartbeat time interval. Bin 2 contains oscillometric blood pressure measurement data for which the associated time interval is less than or equal to the average beat-to-beat time interval.

Thereafter, the oscillometric data in the bin or bins is used to calculate at least one systolic and diastolic blood pressure value in step 122. As noted in U.S. Pat. No. 4,638,810, a systolic and/or diastolic pressure value may be determined by ascertaining the cuff pressure associated with oscillation pulses having a predetermined fractional value of the maximum oscillation pulse value. The measured values may be improved by applying curve-fit or model-fit techniques to the oscillatory envelope, as described in U.S. Pat. No. 5,704,362.

The more extreme blood pressure values, i.e. the highest systolic and the lowest diastolic blood pressure value, will be derived from the data in bin 1. The data in bin 2 is used to compute a lowest value for systolic blood pressure and a highest value for diastolic blood pressure in the same manner as blood pressure values were obtained from the data in bin 1.

One or more of the blood pressure values determined in step 122 may be displayed or otherwise indicated to a clinician in step 124. For example, it is seen as useful to a clinician to display on a monitor the highest and lowest systolic blood pressure values, the highest and lowest diastolic blood pressure values and typical blood pressure values.

It will be appreciated that a minimum amount of oscillometric data is needed in a data bin in order to calculate the blood pressure values. It may occur that during a given non-invasive blood pressure measurement, an insufficient amount of oscillometric data will be sorted into a bin. Should this occur, data from a plurality of blood pressure measurement procedures may be used to provide a sufficient amount of data in the bin.

The data processing steps shown in FIG. 8 may be carried out in an appropriately programmed microprocessor or other computing apparatus to obtain the desired technical effect.

Figure 9:
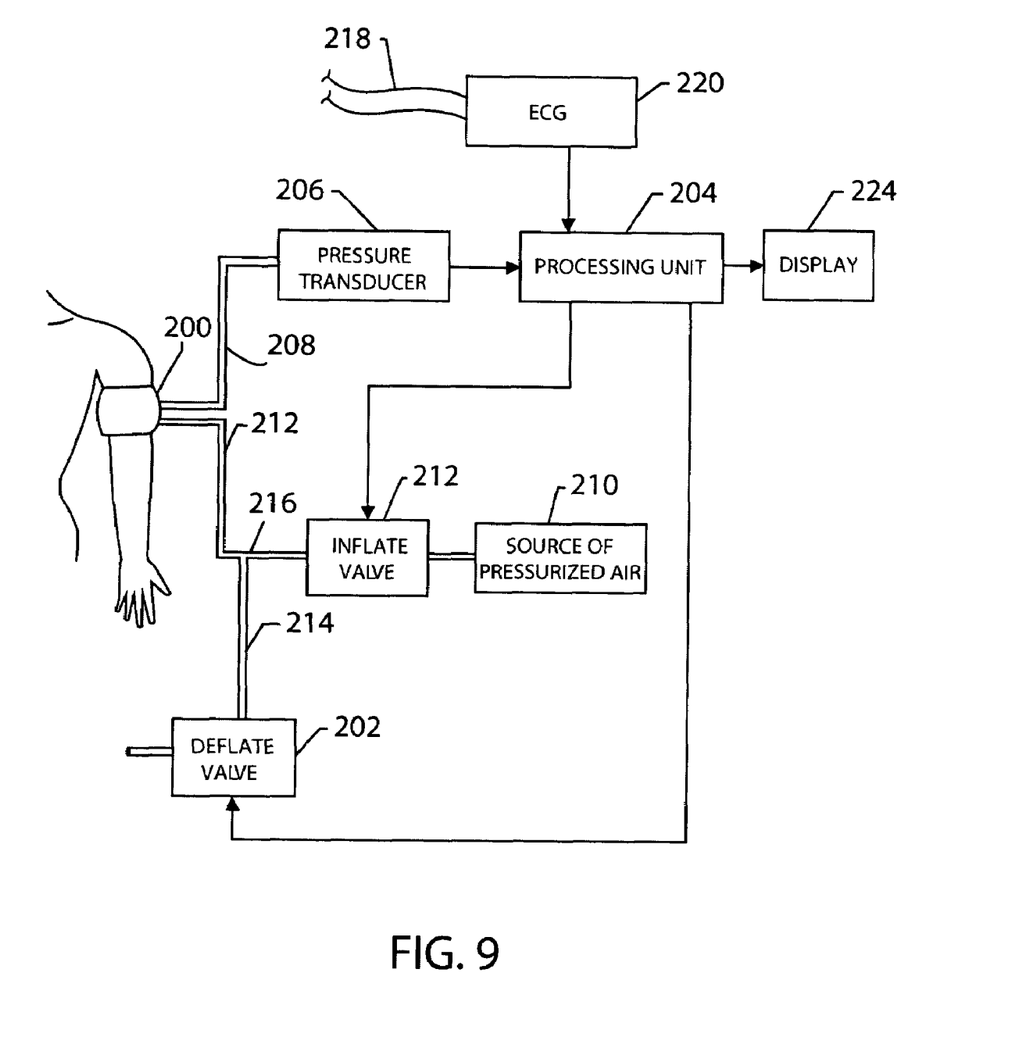
FIG. 9 shows apparatus for practicing the present invention.

Apparatus for practicing the method of the present invention is shown in FIG. 9. The apparatus includes a conventional flexible inflatable and deflatable cuff 200 surrounding the arm of a subject for occluding the brachial artery in the arm when fully inflated. As cuff 200 is decrementally deflated in the manner shown in FIG. 7 using deflate valve 202, the arterial occlusion is relieved in a stepwise fashion. Deflate valve 202 may be controlled by signal processing unit 204 that may comprise a microprocessor.

A pressure transducer 206 is coupled by pneumatic duct 208 to cuff 200 for sensing the pressure in the cuff. In accordance with conventional oscillometric techniques, pressure oscillations in the artery are sensed by changes in the counter pressure of cuff 200 to produce pressure pulses 12, also shown in FIG. 7. The pressure pulses are converted into an electrical signal by transducer 206 and provided to processing unit 204.

Additionally, a source of pressurized air 210 is connected through inflate valve 212 to pressure cuff 200. Inflate valve 210 is electrically controlled from processing unit 204.

Inflate valve 212 is coupled to cuff 200 by pneumatic conduit 214. Deflate valve 202 is connected by duct 216 and branch connection 218 with conduit 214 leading to cuff 200.

The electrocardiographic data shown in FIG. 1 is obtained from ECG electrodes (not shown) applied to the patient and connected to electrode leads 220. The electrode leads are connected to electrocardiograph 222 which is coupled to processing unit 204.

Processing unit 204 may include a microprocessor and appropriate memory and other elements for receiving the electrocardiographic data from electrocardiograph 222 and the oscillatory blood pressure data from pressure transducer 206. The microprocessor is programmed to carry out the processing steps shown in FIG. 8. Processing unit 204 is also connected to display 224 for displaying desired blood pressure values.

Various alternatives and embodiments are contemplated as being within the scope of the following claims particularly pointing out and distinctly claiming the subject matter regarded as the invention.

What is claimed is:

1. A method for obtaining at least one blood pressure value of interest from a non-invasive blood pressure measurement using an oscillometric technique, the blood pressure measurement altering the pressure of an occluder over a measurement time period to vary the extent of occlusion of a blood vessel used for pressure measurement, said method comprising the steps of:
    (a) analyzing the functioning of the heart to obtain physiological data suitable for identifying, in a series of heartbeats in the measurement time period, those heartbeats having blood pressure properties of interest and heartbeats not having blood pressure properties of interest;
    (b) obtaining oscillometric blood pressure measurement data for the heartbeats of the series and associating same to the physiological data;
    (c) establishing at least one criterion for the physiological data that identifies heartbeats in the series of heartbeats having the blood pressure properties of interest;
    (d) applying the criterion to the physiological data to accumulate a subset of the oscillometric blood pressure measurement data for which the associated physiological data meets the criterion; and
    (e) deriving at least one blood pressure value of interest from the accumulated subset of the oscillometric blood pressure measurement data.

2. The method according to claim 1 wherein step (a) is further defined as analyzing the functioning of the heart to obtain physiological data comprising the time interval between sequential heartbeats and step (c) is further defined as establishing a criterion based on the length of the heartbeat-to-heartbeat time interval.

3. The method according to claim 1 wherein step (a) is further defined as analyzing the functioning of the heart to obtain physiological data comprising oscillometric pulse shape data and wherein step (c) is further defined as establishing a criterion based on oscillometric pulse shape.

4. The method according to claim 1 further defined as including the step of obtaining electrocardiographic data, wherein step (a) is further defined as analyzing the morphology of the electrocardiographic data, and wherein step (c) is further defined as establishing a criterion based on electrocardiographic data morphology.

5. The method according to claim 1 wherein step (e) is further defined as deriving at least one extreme blood pressure value.

6. The method according to claim 5 wherein step (e) is further defined as deriving at least one of a high systolic blood pressure value and a low diastolic blood pressure value.

7. The method according to claim 6 wherein step (e) is further defined as deriving a plurality of blood pressure values from the accumulated oscillometric blood pressure measurement data.

8. The method according to claim 5 further including the step of providing at least one typical blood pressure value from the obtained oscillometric blood pressure measurement data.

9. The method according to claim 1 further including the step of providing at least one typical blood pressure value from the obtained oscillometric blood pressure measurement data.

10. The method according to claim 1 wherein step (e) is further defined as deriving a plurality of blood pressure values from the accumulated oscillometric blood pressure measurement data.

11. The method according to claim 1 further defined as using physiological data and oscillometric blood pressure measurement data from a plurality of non-invasive blood pressure measurements.

12. A method for obtaining at least one blood pressure value of interest from a non-invasive blood pressure measurement using an oscillometric technique, the blood pressure measurement altering the pressure of an occluder over a measurement time period to vary the extent of occlusion of a blood vessel used for pressure measurement, said method comprising the steps of:
    (a) analyzing the functioning of the heart to obtain physiological data suitable for identifying, in a series of heartbeats in the measurement time period, those heartbeats having blood pressure properties of interest and heartbeats not having blood pressure properties of interest;
    (b) obtaining oscillometric blood pressure measurement data for the heartbeats of the series and associating same to the physiological data;
    (c) establishing a plurality of criteria for the physiological data that identifies heartbeats in the series of heartbeats having the blood pressure properties of interest;
    (d) applying the plurality of criteria to the physiological data to provide a plurality of accumulations of accumulate oscillometric blood pressure measurement data in accordance with the criteria; and
    (e) deriving at least one blood pressure value of interest from the accumulated oscillometric blood pressure measurement data.

13. The method according to claim 12 wherein step (e) is further defined as deriving at least one blood pressure value from each accumulation of oscillometric blood pressure measurement data.

14. The method according to claim 13 wherein step (e) is further defined as deriving a plurality of blood pressure values from each accumulation of oscillometric blood pressure measurement data.

15. The method according to claim 14 wherein step (e) is further defined as deriving a high systolic blood pressure value and a low diastolic blood pressure value from an accumulation of oscillometric blood pressure measurement data.

16. A method for obtaining extreme blood pressure values from a single non-invasive blood pressure measurement using an oscillometric technique, the blood pressure measurement altering the pressure of an occluder over a measurement time period to vary the extent of occlusion of a blood vessel used for pressure measurement, said method comprising the steps of:
    (a) measuring the time intervals between sequential heartbeats for a series of heartbeats in the measurement time period;
    (b) obtaining oscillometric blood pressure measurement data for the heartbeats of the series and associating same to the heartbeat time intervals;
    (c) determining an average time interval between heartbeats from time interval measurements associated with the measurement time period;
    (d) defining data bins for measured oscillometric blood pressure data in accordance with predetermined properties of the time intervals associated with the blood pressure data to include at least a first bin for blood pressure data associated with time intervals that are longer as compared to the average time interval and a second bin for blood pressure data associated with time intervals that are shorter as compared to the average time interval;
    (e) sorting the measured oscillometric blood pressure data into the data bins in accordance with the associated time intervals;
    (f) deriving at least one of a high systolic blood pressure value and a low diastolic blood pressure value for the blood pressure measurement from the data in a first data bin; and
    (g) deriving at least one of a low systolic blood pressure value and a high diastolic blood pressure value for the blood pressure measurement from the data in a second bin.

17. The method according to claim 16 further including the step of determining typical blood pressure values from the oscillometric blood pressure measurement data.

18. The method according to claim 16 wherein the method is further defined as a method for obtaining blood pressure values under conditions in which the time intervals between sequential heartbeats is irregular.

19. The method according to claim 16 wherein step (c) is further defined as determining the average time interval from a series of heartbeats in the measurement time period.

20. The method according to claim 16 wherein step (a) is further defined as measuring the time intervals of a predetermined number of heartbeats and step (c) is further defined as determining the average time interval from the time intervals for the predetermined number of heartbeats.

21. The method according to claim 16 further defined as obtaining blood pressure values from a plurality of blood pressure measurements and wherein steps (a) and (b) are further defined as measuring time intervals and obtaining oscillometric blood pressure measurement data for an additional measurement period, and wherein step (e) is further defined as sorting measured oscillometric blood pressure data from at least one additional period into at least one of the data bins.

22. The method according to claim 16 wherein step (b) is further defined as associating the blood pressure measurement data with the immediately preceding heartbeat time interval.

23. The method according to claim 16 wherein step (b) is further defined as obtaining occluder pressurization data and blood pressure oscillometric pulse amplitude data.

24. The method according to claim 16 wherein step (d) is further defined as defining a first data bin for blood pressure data for which the associated time intervals are equal to or greater than the average time interval and a second data bin for blood pressure data for which the associated time intervals are equal to or less than the average time interval.

25. The method according to claim 16 where step (d) is further defined as defining data bins on the basis of statistical properties of the measured time intervals.

26. The method according to claim 25 wherein step (d) is further defined as defining at least a first data bin for blood pressure data for which the associated time interval falls between the average time interval and a given number of standard deviations on one side of the average time interval value and at least a second data bin for blood pressure data for which the associated time interval falls between the average time interval and a given number of standard deviations on the other side of the average time interval value.

27. The method according to claim 25 wherein step (d) is further defined as defining a number of data bins greater than two.

28. The method according to claim 16 wherein at least one of steps (f) and (g) is further defined as applying mathematical curve-fit or model-fit techniques to the oscillometric blood pressure measurement data.

29. The method according to claim 16 further defined as outputting selected systolic and diastolic blood pressure values.

30. Apparatus for obtaining at least one blood pressure value of interest from a non-invasive blood pressure measurement using an oscillometric technique, the blood pressure measurement altering the pressure of an occluder over a measurement time period to vary the extent of occlusion of a blood vessel used for pressure measurement, said apparatus comprising:
   means for obtaining physiological data suitable for distinguishing, in a series of heartbeats in the measurement time period, those heartbeats having blood pressure properties of interest from heartbeats not having blood pressure properties of interest;
   means couplable to said occluder for obtaining oscillometric blood pressure measurement data for the heartbeats of the series;
   means for associating the oscillometric to the physiological data;
   means for establishing at least one bin to contain blood pressure measurement data having the blood pressure properties of interest;
   means for applying at least one criterion to the physiological data to accumulate oscillometric blood pressure measurement data for which the associated physiological data meets the criteria; and
   means for deriving at least one blood pressure value of interest from the accumulated oscillometric blood pressure measurement data.

31. The apparatus according to claim 30 wherein said means for obtaining physiological data is further defined as obtaining physiological data comprising the time intervals between sequential heartbeats and wherein said means for establishing at least one bin establishes at least one bin based on the length of the heartbeat-to-heartbeat time interval.

32. The apparatus according to claim 31 wherein said means for establishing at least one bin defines a first data bin for accumulating blood pressure data for which associated time intervals are equal to or greater than an average time interval and a second data bin for accumulating blood pressure data for which the associated time intervals are equal or less than the average time interval and said deriving means is further defined as deriving at least one blood pressure value from the data in at least one of the bins.

33. The apparatus according to claim 32 wherein said means for establishing is further defined as defining a number of data bins greater than two.

34. The apparatus according to claim 30 wherein said deriving means is further defined as deriving at least one extreme blood pressure value.

35. The apparatus according to claim 34 wherein said deriving means is further defined as deriving at least one of a high systolic blood pressure value and a low diastolic blood pressure value.

36. The apparatus according to claim 30 wherein said deriving means is further defined as deriving a plurality of blood pressure values from the accumulated oscillometric blood pressure measurement data.

37. The apparatus according to claim 30 wherein said means for establishing at least one bin establishes a plurality of bins and wherein said applying means applies a plurality of criteria to the physiological data to provide a plurality of accumulations of oscillometric blood pressure measurement data in accordance with the criteria.

38. The apparatus according to claim 37 wherein said deriving means is further defined as deriving at least one blood pressure value from each accumulation of oscillometric blood pressure measurement data.

39. The apparatus according to claim 30 wherein said means for obtaining physiological data is further defined as obtaining physiological data comprising oscillometric pulse shape data and wherein said means for establishing a criterion establishes a criterion based on oscillometric pulse shape.

40. The apparatus according to claim 30 wherein said means for obtaining physiological data is further defined as means for obtaining electrocardiographic data and wherein said means for establishing a criterion establishes a criterion based on electrocardiographic data morphology.

41. The apparatus according to claim 30 further defined as having means for outputting selected systolic and diastolic blood pressure values.

* * * * *